United States Patent
Sanchez

[11] Patent Number: 6,152,147
[45] Date of Patent: Nov. 28, 2000

[54] DENTAL FLOSS HOLDER

[76] Inventor: Maria Sanchez, 961 SW. 109th Ave., Pembroke Pines, Fla. 33025

[21] Appl. No.: 09/370,173

[22] Filed: Aug. 9, 1999

[51] Int. Cl.[7] .......................... A61C 15/00; A61B 19/02; B65D 85/00
[52] U.S. Cl. .................... 132/324; 132/323; 206/63.5; 206/388
[58] Field of Search ................... 132/324, 323, 132/321, 328; 206/63.5, 565, 388; 221/312 C; 225/34

[56] References Cited

U.S. PATENT DOCUMENTS

| | | |
|---|---|---|
| 2,083,398 | 6/1937 | Rohland . |
| 2,656,131 | 10/1953 | Johnson . |
| 2,692,676 | 10/1954 | Grover .................................. 206/63.5 |
| 2,929,541 | 3/1960 | Castelli et al. . |
| 2,962,156 | 11/1960 | Adams .................................. 206/63.5 |
| 2,977,033 | 3/1961 | Jones . |
| 3,080,963 | 3/1963 | Rothgart ............................... 206/63.5 |
| 3,138,244 | 6/1964 | White .................................... 206/63.5 |
| 3,388,790 | 6/1968 | Slomczewski ........................ 206/63.2 |
| 3,490,725 | 1/1970 | Speelman .............................. 206/63.5 |
| 3,616,096 | 10/1971 | Roeder ................................. 206/63.5 |
| 3,624,161 | 11/1971 | Bub ....................................... 206/63.5 |
| 3,696,920 | 10/1972 | Lahay ................................... 206/63.2 |
| 3,759,376 | 9/1973 | Lisowski . |
| 3,819,039 | 6/1974 | Erickson ............................... 206/388 |
| 4,073,419 | 2/1978 | Tarrson et al. . |
| 4,191,291 | 3/1980 | Brown . |
| 4,327,755 | 5/1982 | Endelson . |
| 4,807,752 | 2/1989 | Chodorow ............................ 132/324 |
| 4,895,249 | 1/1990 | Davis et al. . |
| 5,074,100 | 12/1991 | Lepie . |
| 5,086,914 | 2/1992 | Mish et al. ............................ 206/63.3 |
| 5,112,297 | 5/1992 | Stalcup et al. ........................ 604/1 |
| 5,156,311 | 10/1992 | Spencer, Jr. et al. . |
| 5,282,563 | 2/1994 | Oliver et al. . |
| 5,322,077 | 6/1994 | Corella ................................. 132/323 |
| 5,396,991 | 3/1995 | Lachambre . |
| 5,421,457 | 6/1995 | Listenberger ........................ 206/388 |
| 5,490,722 | 2/1996 | Sonnett et al. . |
| 5,566,692 | 10/1996 | Thornton .............................. 132/324 |
| 5,649,625 | 7/1997 | Ovadia . |
| 5,913,418 | 6/1999 | Singh ..................................... 132/324 |
| 5,947,132 | 9/1999 | Swanson ............................... 132/324 |

*Primary Examiner*—John J. Wilson
*Assistant Examiner*—Robyn Kieu Doan
*Attorney, Agent, or Firm*—Malloy & Malloy, P.A.

[57] ABSTRACT

A holder assembly for removably storing a plurality of individual dental floss products of the type which typically comprise a looped configuration at one end thereof and which are designed primarily but not exclusively for use in the flossing or cleaning of bridgework or other orthodontic appliances, wherein the holder assembly comprises a base including a plurality of apertures at least some of which include a retaining structure cooperatively dimensioned, disposed and configured with corresponding ones of the apertures to removably maintain and orient the looped dental floss products in an upright or outwardly extending position thereby rendering the dental floss products readily accessible for use by a dental hygienist or other personnel during the flossing process. A receiving structure may also be provided comprising a chamber assembly in the form of a plurality of chambers disposed in aligned relation with at least some of the plurality of apertures and wherein the chambers are disposed and configured to receive preferably the looped end of the floss product therein and facilitate the removable storage in the aforementioned upright and/or outwardly extending, readily accessible orientation.

13 Claims, 2 Drawing Sheets

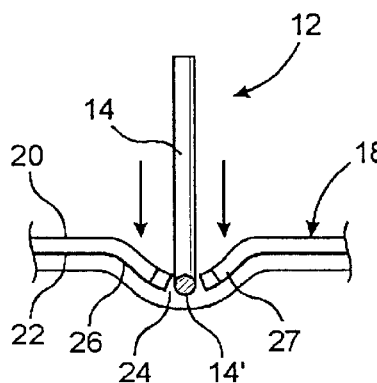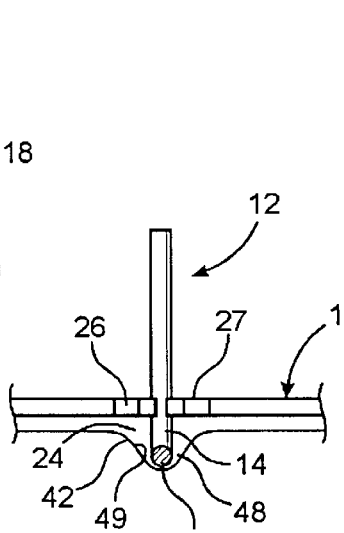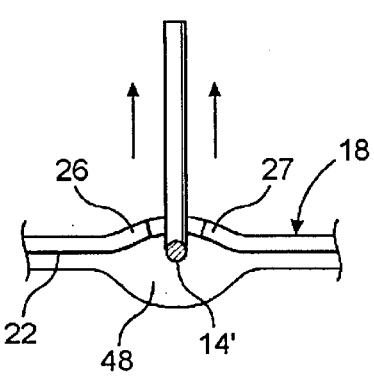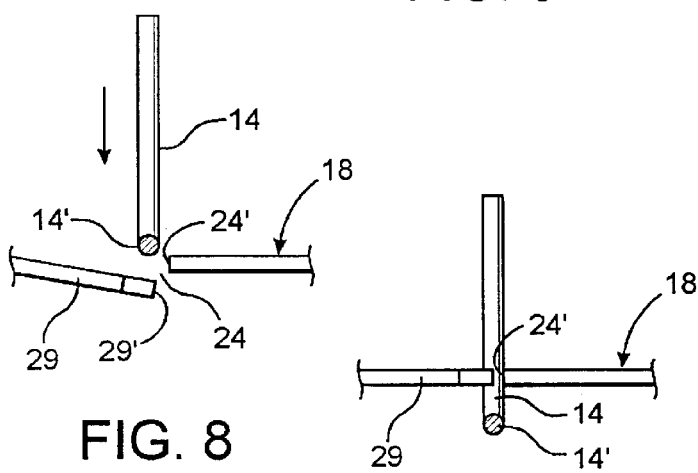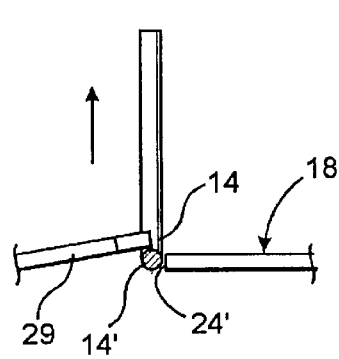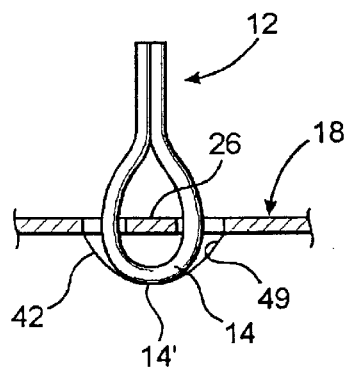

DENTAL FLOSS HOLDER

BACKGROUND OF THE INVENTION

1. Field of the Invention

This invention relates to a holder assembly for removably storing a plurality of dental floss products commonly known as floss threaders which are distinguishable from normal, elongated strands of dental floss by having a looped configuration at one end thereof. The holder assembly is structured to maintain a plurality of individual dental floss products or "floss threaders" in an outwardly extending, readily accessible orientation so as to facilitate access thereto by personnel using such products.

2. Description of the Related Art

The use of dental floss is well-known and extensive both by individuals when cleaning their own teeth and gums and also by professionals, such as dental hygienists, when performing a detailed cleaning and flossing process during periodic visits to the dentist. In either instance, dental floss is typically available in packages containing a single strand of floss having an extended length of twenty-five feet or more wound or otherwise collected into a compact configuration. This type of elongated dental floss product is typically sold in packages or dispensers which facilitate the removal of a relatively short length of generally six to twelve inches. The length of floss removed from the package is cut by a blade or similar structure normally found on the package or dispenser itself.

The packaging art comprises a large variety of different packaging structures specifically designed for the storage and dispensing of conventional strand dental floss, wherein the main supply of dental floss is maintained in some type of compact configuration in order to avoid tangling of the elongated floss strand which would render it difficult or impossible for efficient removal when required for use. The design and structure of such dental floss packaging varies greatly and includes plastic or other relatively rigid material containers as well as paper containers which are opened by the removal of tear-away sections.

In addition, while the use of the elongated strands of dental floss is well suited for most situations, there are times when it is preferable to use precut, individual floss segments. In the latter category such shorter or smaller segments are normally packaged individually or stored in relatively small numbers. The packaging of the shorter floss segments is designed to accommodate use by professional hygienists as well as rendering the use of such segments more convenient for individuals by facilitating storage in the home, when travelling or when it is desired to carry dental floss in a pocket book, purse, wallet, etc.

One further category of relatively specialized dental floss products are known as "floss threaders". Floss threaders are characterized by a relatively short length of dental floss having a fixed loop configuration at one end. This type of looped dental floss product or "floss threader" is designed to facilitate the threading of elongated strands of dental floss under bridges, dental splints and/or other orthodontic appliances in order to properly position the more conventional, elongated strands of dental floss in a proper or intended position to accomplish flossing or cleaning using conventional flossing techniques. Looped floss threaders of the type referred to above are commercially available under the trademark "EEZ-THRU"® manufactured by the John O. Butler Co. of Chicago, Ill. The practice of using such looped floss threaders starts with the cutting or otherwise separation of approximately 18" inches of an elongated floss strand stored or packaged in conventional fashion. Four to five inches of the floss strand are passed through the looped end of the floss threader. The opposite end of the floss threader, typically having an elongated, straight line configuration is passed or "threaded" through spaces between or under the teeth or dental appliance being cleaned. While floss threaders of the type referred to are formed of a flaccid material, they are structured to include a somewhat greater rigidity in order to allow or facilitate the positioning of the straight line end of the floss threader through the space between or under the teeth or appliance being cleaned, as set forth above.

Floss threaders of the type referred to are not normally included in a customary "dental set-up" used by professional personnel. However, floss threaders are commercially available in packaging. Due to the thinness and general small size of such floss threaders, and the fact that the technician is wearing gloves, the removal from the package and the separation of individual ones of such floss threaders is extremely difficult and often results in the dropping of all the floss threaders from the package. Therefore, packaging of the type set forth above does not facilitate the efficient dispensing of individual floss threaders especially while the dental hygienist or other individual is performing the actual cleaning procedure. In doing so, the user may consecutively utilize a number of such floss threaders on a somewhat repetitive basis. The packaging in which such products are normally purchased and supplied does not facilitate the efficient repetitive dispensing of individual ones of a plurality of floss threaders. In addition, the relatively small size and thin gauge of the material from which the floss threaders are formed makes them somewhat difficult to be individually picked up from a flat surface such as when a number of the floss threaders are spread or inadvertently dropped on a horizontal surface such as an instrument tray or the like.

Based on the above, there is a significant need in this area for a holder assembly specifically designed to removably store and maintain a plurality of individual dental floss segments or products, such as but not limited to looped dental floss threaders, in a readily accessible orientation which facilitates the individual selection and removal of such products for use on a substantially repetitive basis. Such an improved holder assembly should be structurally adapted for use by professionals and other individuals in a variety of locations and particularly wherein the improved dental floss holder assembly takes advantage of the physical and structural characteristics of the individual floss threaders or like dental floss products being utilized.

SUMMARY OF THE INVENTION

The present invention is directed to a holder assembly designed to removably store a plurality of individual dental floss products, such as, but not limited to dental floss threaders of the type having one end formed into a looped configuration, and wherein the individual dental floss products are maintained in a readily accessible orientation to facilitate easy access thereto in a manner which will not delay or significantly interrupt the cleaning process when the plurality of dental floss products are being repeatedly used.

More specifically, the holder assembly of the present invention comprises a base. The base includes an exposed surface and preferably an oppositely disposed undersurface. Moreover, extending from the exposed surface towards the exposed undersurface are a plurality of apertures. Disposed in overlying, at least partially covering relation to preferably each one of said plurality of apertures are a plurality of retaining structures. The retaining structures are preferably mounted and/or integrally formed on the base.

Depending upon the particular embodiment, to be discussed in greater detail hereinafter, at least some of the plurality of apertures are cooperatively structured, configured and dimensioned with at least one of the retaining structures. As a result, the one or more retaining structures associated with each of the plurality of apertures are disposed in substantially overlying relation thereto. Furthermore, the dimension and configuration of each of the retaining structures relative to one another and to the dimension and configuration of the aperture itself, serves to somewhat restrict, but still allow the "controlled" passage of a dental floss product therethrough.

When the holder assembly of the present invention is used for the removable storage and orientation of a plurality of looped floss threaders, the plurality of apertures and associated plurality of retaining structures are cooperatively configured and dimensioned to have the looped end of the floss threader pass therethrough. Once inserted within the apertures, the individual floss threaders extend outwardly therefrom in an upright or otherwise preferred orientation such that the opposite end or straight line end of the floss threaders are readily accessible in spaced relation above the exposed surface of the base. This orientation, as will be apparent hereinafter, greatly facilitates the individual removal of the floss threaders from their stored position within the floss holder assembly generally, and the base specifically.

In order to further facilitate the orientation of individual ones of the plurality of dental floss products in an outwardly extending, readily accessible position, additional structural features of the holder assembly of the present invention may include the provision of a receiving structure comprising a chamber assembly located adjacent to or contiguous with the undersurface of the base. More specifically, the chamber assembly comprises a plurality of chambers each of which is disposed in substantially aligned, receiving relation to one of said plurality of apertures formed in said base, such that the individual floss threaders or other floss products, passing through the plurality of apertures will be received and at least partially supported within the corresponding ones of the plurality of chambers. In particular, when the holder assembly is specifically designed to removably store floss threaders having one end formed into a looped configuration, the inner surface portions of the plurality of chambers preferably have a substantially curved configuration which at least partially conforms to the overall looped configuration of the floss threaders. Further, the thickness, depth and other significant dimensional characteristics of each of the chambers may be varied so as to facilitate the support of the end of the dental floss products or floss threaders inserted through the individual apertures in the base.

It is further emphasized that the above described retaining assembly and the receiving structure can be structurally adapted for use in combination with one another or used separately or independently of one another by incorporating whatever structural modifications necessary to maintain the individual dental floss products in the preferred outwardly extending and/or upright readily accessible orientation. By way of example only, such structural modifications may include a variance in the dimension, disposition, configuration and relative placement of the one or more retaining members associated with each aperture and/or the individual chambers associated with each aperture in order to best facilitate utilization of the retaining structure and the receiving structure in combination with one another and independently of one another.

BRIEF DESCRIPTION OF THE DRAWINGS

For a fuller understanding of the nature of the present invention, reference should be had to the following detailed description taken in connection with the accompanying drawings in which:

FIG. 4 is a side view of the embodiment of FIG. 3 during insertion of the dental floss product;

FIG. 5 is a side view of the embodiment of FIG. 3 retaining the dental floss product;

FIG. 6 is a side view of the embodiment of FIG. 3 during removal of the dental floss product;

FIG. 8 is a side view of the embodiment of FIG. 7 during insertion of the dental floss product;

FIG. 9 is a side view of the embodiment of FIG. 7 retaining the dental floss product;

FIG. 10 is a side view of the embodiment of FIG. 7 during removal of the dental floss product; and FIG. 11 is a front view in partial cutaway of the present invention.

Like reference numerals refer to like parts throughout the several views of the drawings.

DETAILED DESCRIPTION OF THE PREFERRED EMBODIMENT

Figure 1:
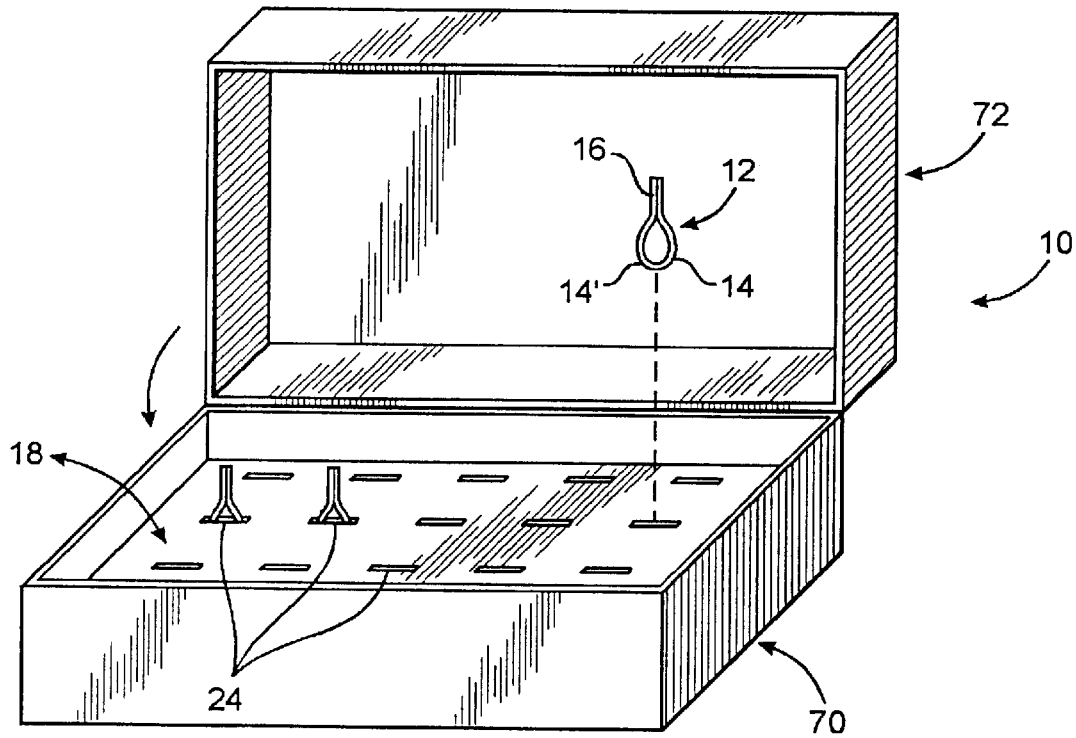
FIG. 1 is a perspective view of a holder assembly of the present invention and a plurality of dental floss products which, in the embodiment shown, may comprise looped floss threaders.

As shown in the accompanying Figures, the present invention is directed towards a holder assembly, generally indicated as 10. The holder assembly 10 is preferably designed and structured to removably contain a plurality of individual dental floss products, generally indicated as 12, in a convenient and readily accessible manner. While the holder assembly 10 of the present invention is designed to hold a variety of different dental floss products, the particular dental floss product 12 is preferably in the form of a "floss threader" characterized by one end 14 having a continuous, looped configuration, and the opposite end, as at 16, having a substantially singular configuration. Furthermore, the material from which the dental floss product or looped floss threader 12 is formed is sufficiently flexible to be easily manipulable to facilitate its positioning and use in the intended manner. However, the floss threader 12 is also formed of a material structured to have sufficient rigidity or structural integrity to be maintained in an upright and/or outwardly extending position which facilitates the individual selection, gripping and removal of each of the plurality of floss threaders 12 from their stored position, as shown in FIG. 1. This somewhat additional amount of rigidity also facilitates the positioning of the floss threader 12 in the intended manner by passing or threading the end 16 through spaces between the teeth or dental appliances affixed within the mouth of a patient.

More specifically, the holder assembly 10 of the present invention comprises a base 18 including an outer exposed surface 20 and preferably, but not necessarily, an undersurface 22 disposed in generally opposing relation to one another. Further, as shown in the various Figures, the base 18 has a plurality of apertures formed therein and extending preferably through the exposed surface 20 of the base 18. Each of the plurality of apertures are preferably disposed in spaced apart relation to one another in an array of any preferred configuration. Moreover, each of the plurality of apertures 24 are dimensioned and configured to allow passage therethrough of at least one end, preferably the looped end 14, of the floss threader 12.

Figure 3:
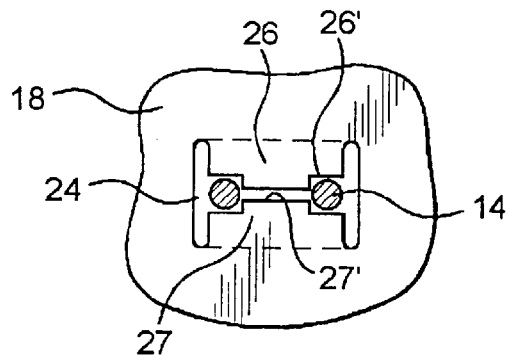
FIG. 3 is a top detailed view in partial cutaway of certain structural features of the embodiment of FIG. 1.

Another feature of the present invention is the provision of a retaining structure which, in the embodiment of FIGS. 3–5 includes at least one retaining member 26 but preferably a plurality of such retaining members as at 26 and 27. The retaining members are cooperatively positioned to at least partially restrict passage of the floss threader 12, and particularly the looped end 14 thereof, through the apertures 24 when being inserted into the aperture 24, as shown in FIG. 4, and/or removed therefrom, as shown in FIG. 6. In another embodiment of the present invention, to be described in greater detail hereinafter, only a single retaining member 29 is associated with each of the plurality of apertures 24 and is correspondingly dimensioned and configured so as to be disposed in a normally covering relation to the aperture 24.

Again with primary reference to the embodiment of FIGS. 3–6, each of the retaining members 26 and 27, may be formed from a flexible material of substantial rigidity such that they are normally disposed in the aforementioned co-planar relation as represented best in FIGS. 3 and 5, or of a generally rigid material having at least one generally flexible seam. Each of the retaining members 26 and 27 may be integrally formed with a remainder of the base 18 so as to be positioned in co-planar relation therewith or alternately may be fixedly or otherwise attached so as to extend inwardly towards one another generally from opposite peripheral portions or edges of the aperture 24. The retaining members 26 and 27 may be spaced from one another as shown in FIG. 3 along an inwardly extending peripheral edge 26' and 27', respectively. Furthermore, each of the retaining members 26 and 27 are preferably structured to demonstrate sufficient flexibility to be capable of being forced out of co-planar relation to the aperture 24 thereby serving to space the retaining members 26 and 27 a greater distance from each other in order to allow passage therethrough of the end 14 of one of the dental floss products or floss threaders 12. As shown in FIG. 4, a downward force exerted on one or both of the retainer members 26 and 27, such as by the user's finger, causes a separation thereof and allows the end 14 to pass through the aperture 24 beyond the retaining members 26 and 27. The outermost extremity 14' of the end portion 14 as a well as certain amount of the length of end 14 connected thereto thereby passes beneath the base 18 beyond the undersurface 22. Removal of the floss threader 12 is best shown in FIG. 6 and is accomplished merely by exerting a pulling force thereon which forces the extremity 14' through the spacing existing between the correspondingly positioned peripheral edges of the retaining members 26 and 27 causing an outwardly directed flexure thereof.

When the floss threader 12 is in its removably stored position, as shown in FIGS. 3 and 5, at least a portion of the innermost peripheral edges of the respective retaining members 26 and 27 may be at least partially surrounded by the continuous closed looped configuration of the end 14, as shown, or a generally sandwiching captivation may be achieved by the retaining members 26 and 27 on the upwardly and outwardly depending portions of the end 14 so as to hold the floss threader. The dental floss threader 12 is thereby maintained in the preferred upright or outwardly extended position such that the free end 16 extends outwardly from the outer exposed surface 20 of base 18 thereby facilitating their gripping and removal in the manner set forth above.

Figure 7:
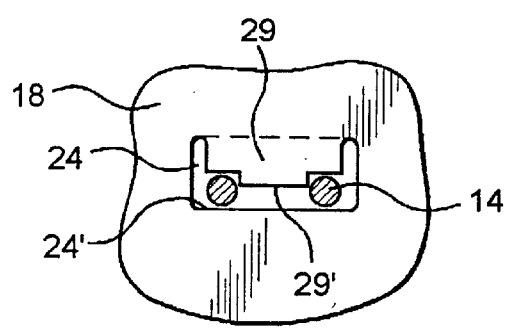
FIG. 7 is another embodiment of certain structural features of the holder assembly differing from the embodiment of FIGS. 3–6.

In the embodiment of FIG. 7, a single retaining member 29 is disposed in a preferred co-planar relation to the base as well as being disposed in overlying at least partially covering relation to the aperture 24. Passage of the floss threader 12, and particularly, the looped end 14, through the aperture 24 is restricted due to the fact that the peripheral edges as at 29' are closely positioned relative to the peripheral portion 24' of the aperture 24. Accordingly, a force exerted downwardly on the retaining element 29, such as by the user's finger, will cause an enlargement of the spacing between the peripheral edges 29' and 24' as best shown in FIG. 8 and facilitate the insertion of the end portion 14 through the aperture 24 and beneath the undersurface 22 of the base 18. FIG. 9 shows the end portion 14 of the floss threader 12 disposed in its removable but preferred stored orientation, extending through the base 18 and aperture 24. FIG. 10 shows the upward or outward flexure or forced positioning of the retaining element 29 upon a pulling force being exerted on the floss threader 12 as the end 14, and particularly, the extremity 14' is forced through the spacing between the corresponding peripheral edges 29' and 24' of the retaining member 29 and the aperture 24, respectively.

Figure 2:
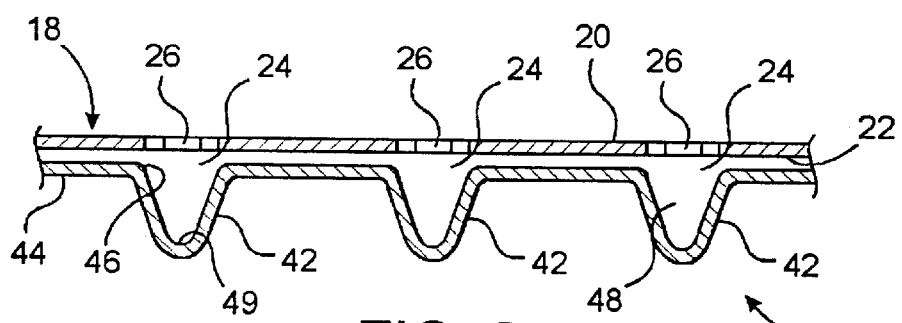
FIG. 2 is a sectional view of the embodiment of FIG. 1.

Yet another embodiment of the present invention is shown in the attached Figures and comprises the inclusion of a receiving portion generally indicated as 40 in FIG. 2. The receiving portion 40 comprises a chamber assembly preferably defined by a plurality of individual chambers 42 disposed in inwardly extending and/or depending relation to a support member 44. The support member 44 is mounted immediately adjacent to or contiguous with the undersurface 22 of the base 18 and may be integrally, fixedly or otherwise secured to the base or to a housing or support structure 70, shown in FIG. 1 and to be described in greater detail hereinafter. Indeed, the base 18 and support member 44 may be a single element defining an open area therebeneath and/or a solid element with the chambers 42 defined therein.

The receiving assembly 40 is structured such that each of the chambers 42 has an open end 46 which is preferably disposed in direct communication with a substantially hollow interior 48. Further, the open end 46 and hollow interior 48 of each of the receiving chambers 42 are disposed in direct aligned, receiving relation with the various apertures 24, such that the dental floss products or floss threaders 12 generally, and the end 14 particularly, are received within the hollow interiors 48 of the chambers 42 when they pass through the apertures 24.

Another structural feature of the receiving assembly 40 is the inner surface portion 49 of each of the chambers 42 having a preferably curved configuration which at least partially corresponds to the curved extremity 14' of the continuously closed loop configuration of the end 14 of the floss threader 12. As shown in FIG. 11, the length of each chamber 42 extends substantially along at least a majority of the length of the aperture 24 such that the extremity 14' of each of the floss threaders 12 may be at least partially supported on the interior surface 49. This at least partial support by the interior surface 49 of each of the chambers 42 facilitates each of the inserted floss threaders 12 being maintained in the preferred upright, outwardly extending orientation which disposes the free ends 16 of each of the floss threaders 12 in a readily accessible position for removal by exerting a pulling force thereon as explained above.

It is to be emphasized that the intended spirit and scope of the present invention is meant to include the use of a base 18 with the retaining structure in combination with the receiving assembly 40, or alternately, the retaining structure and the receiving assembly 40 may be used independently of one another.

With reference to FIG. 1, another structural feature of the present invention is the preferred mounting or support of the base 18 in a housing or similar support structure generally indicated as 70. The housing 70, base 18 and other of the structural components of the holder assembly 10, may be pre-sterilized and/or be originally packaged in a sterilized outer container or like structure. A closure assembly generally indicated as 72 may be movably attached or mounted relative to the base 18 so as to be selectively positionable in overlying, enclosing relation thereto, as well as the plurality of floss threaders 12 or other dental floss products maintained on the base 18. The housing 70 and closure assembly 72 facilitates storage and transportation of a plurality of the floss threaders 12 which have previously been inserted through the various apertures 24 in the base 18 in the manner set forth above.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly for removably containing dental floss products, said assembly comprising:
   a) a plurality of elongated looped dental floss products,
   b) a base including an exposed surface and a plurality of apertures formed in said exposed surface in substantially co-planar relation thereto,
   c) at least one retaining member disposed in cooperative relation with different ones of said plurality of apertures so as to restrict passage of said dental floss products therethrough, and
   d) said retaining member cooperatively dimensioned and configured relative to the corresponding one of said plurality of apertures to be positioned within and in surrounded relation by a loop portion of the looped dental floss product.

2. An assembly for removably containing dental floss products, said assembly comprising:
   a) a plurality of elongated, looped dental floss products,
   b) a base including an exposed surface and a plurality of apertures formed in said exposed surface in substantially co-planar relation thereto,
   c) a receiving structure including a chamber assembly disposed in underlying relation to said base and in communicating relation with said plurality of apertures,
   d) said chamber assembly comprising a plurality of chambers each disposed in aligned relation to a different one of said plurality of apertures,
   e) at least one retaining member disposed in cooperative relation with different ones of said plurality of apertures so as to restrict passage of said plurality of dental floss products therethrough, and
   e) said plurality of chambers and corresponding ones of said retaining members cooperatively disposed with corresponding ones of said apertures to receive a loop portion of said plurality of dental floss products and facilitate maintenance of said plurality of dental floss products in an outwardly extending, substantially upright orientation relative to said exposed surface.

3. An assembly as recited in claim 2 wherein each of said plurality of chambers comprises a substantially curvilinear configuration at least partially corresponding to one end portion of the dental floss product.

4. An assembly as recited in claim 2 wherein said chamber assembly comprises a plurality of chambers each disposed in aligned receiving relation with a different one of said plurality of apertures.

5. An assembly as recited in claim 4 wherein each of said plurality of chambers is dimensioned and configured to supportively engage the loop portion of said dental floss product to facilitate maintenance thereof in a substantially upright orientation.

6. An assembly as recited in claim 5 wherein each of said plurality of chambers comprises a substantially curvilinear configuration at least partially corresponding to the loop portion of said dental floss product.

7. An assembly as recited in claim 2 wherein said retaining member extends inwardly from a periphery of the corresponding one of said apertures in substantially overlying, at least partially covering relation thereto.

8. An assembly as recited in claim 7 wherein said retaining member is flexible and forcibly positionable out of a co-planar relation to the corresponding one of said plurality of apertures.

9. An assembly as recited in claim 8 wherein said retaining member is cooperatively dimensioned and configured relative to the corresponding one of said plurality of apertures to be positioned within and in surrounded relation by the loop portion of the looped dental floss product.

10. An assembly as recited in claim 9 wherein said retaining member is integrally defined with said base along a periphery of the corresponding one of said plurality of apertures.

11. An assembly as recited in claim 2 wherein said retaining structure comprises a plurality of retaining members collectively disposed in interruptive relation to passage of the loop portion of said dental floss product through a corresponding one of said plurality of apertures.

12. An assembly as recited in claim 11 wherein said retaining structure comprises at least two retaining members extending inwardly from spaced apart peripheral portions of the corresponding one of said plurality of apertures towards one another.

13. An assembly as recited in claim 2 further comprising a closure assembly movably mounted relative to said base and dimensioned and disposed to be selectively positionable in overlying, covering relation to said base.

* * * * *